US009735841B2

(12) United States Patent
Seremjian et al.

(10) Patent No.: US 9,735,841 B2
(45) Date of Patent: Aug. 15, 2017

(54) METHOD AND APPARATUS FOR IDENTIFYING AND TRACKING BIOLOGICAL FLUIDS USING RFID

(71) Applicant: Midwest Medical Technologies of America, LLC, Kenosha, WI (US)

(72) Inventors: Kip Seremjian, Kenosha, WI (US); Clive Hohberger, Highland Park, IL (US); Phillip Houtz, West Lafayette, IN (US); Jonathan Yeazel, Atlanta, GA (US); Fred Kaplan, Bannockburn, IL (US)

(73) Assignee: MIDWEST MEDICAL TECHNOLOGIES OF AMERICA, LLC, Kenosha, WI (US)

( * ) Notice: Subject to any disclaimer, the term of this patent is extended or adjusted under 35 U.S.C. 154(b) by 84 days.

(21) Appl. No.: 14/919,370

(22) Filed: Oct. 21, 2015

(65) Prior Publication Data

US 2016/0113721 A1    Apr. 28, 2016

Related U.S. Application Data

(60) Provisional application No. 62/067,661, filed on Oct. 23, 2014.

(51) Int. Cl.
| | | |
|---|---|---|
| G08C 19/16 | (2006.01) |
| H04B 5/00 | (2006.01) |
| A61B 19/00 | (2006.01) |
| A61J 1/16 | (2006.01) |
| G07F 17/00 | (2006.01) |
| A61J 1/10 | (2006.01) |
| F25D 29/00 | (2006.01) |

(52) U.S. Cl.
CPC .......... *H04B 5/0062* (2013.01); *A61B 19/44* (2013.01); *A61J 1/16* (2013.01); *G07F 17/0092* (2013.01); *A61B 2019/448* (2013.01); *A61J 1/10* (2013.01); *A61J 2205/60* (2013.01); *F25D 29/00* (2013.01); *F25D 2700/02* (2013.01); *F25D 2700/08* (2013.01)

(58) Field of Classification Search
CPC ...... A61B 19/44; A61B 2019/448; A61J 1/10; A61J 1/16; A61J 2205/60; F25D 2700/02; F25D 2700/08; F25D 29/00; G07F 17/0092; H04B 5/0062
See application file for complete search history.

(56) References Cited

U.S. PATENT DOCUMENTS

| 6,116,461 A | 9/2000 | Broadfield et al. |
| 8,567,663 B2 | 10/2013 | Seremjian |
| 8,905,297 B2 | 12/2014 | Seremjian |

(Continued)

OTHER PUBLICATIONS

Dong Wook Lee, International Search Report for Associated PCT Application PCT/US2015/056854, Feb. 5, 2016, Korean Intellectual Property Office, Daejeon, Republic of Korea.

(Continued)

*Primary Examiner* — Omeed Alizada
(74) *Attorney, Agent, or Firm* — Babcock IP, PLLC (57) ABSTRACT

A system and method of tracking, assigning and releasing biological fluids. The system and method identifies, assigns and releases biological fluid products from controlled storage based on medical criteria supported by the use of RFID technology.

16 Claims, 6 Drawing Sheets

(56) References Cited

U.S. PATENT DOCUMENTS

| | | |
|---|---|---|
| 2004/0046020 A1 | 3/2004 | Andreasson et al. |
| 2006/0079994 A1* | 4/2006 | Chu .................... A61G 12/001 700/231 |
| 2008/0024301 A1 | 1/2008 | Fritchie et al. |
| 2008/0208750 A1 | 8/2008 | Chen |
| 2008/0316045 A1 | 12/2008 | Sriharto et al. |
| 2014/0263389 A1* | 9/2014 | Perozek .................... A61J 7/02 221/1 |

OTHER PUBLICATIONS

Briggs, Lynne and Clive Hohberger, iTRACE™ Vein-to-Vein Implementation of HF RFID in Blood Collection through Transfusion. Presentation at RFID in Healthcare; Boston; Sep. 2012.

FDA letter of May 28, 2013 to SysLogic, Inc. approving Section 510(k) application BK120067 and authorizing marketing of iTrace™ for Blood Centers v1.0.924.0.

ICCBBA.org ISBT 128 Standard Technical Specification Version 5.3.0, Jul. 2015.

Knels, Ralf, editor. Guidelines for the Use of RFID Technology in Transfusion Medicine, V 1.0. Vox Sanguinis 98, Supplement 2, Apr. 2010.

* cited by examiner

FIG. 8

METHOD AND APPARATUS FOR IDENTIFYING AND TRACKING BIOLOGICAL FLUIDS USING RFID

RELATED US APPLICATION DATA

This application claims the benefit of U.S. Provisional Patent Application Ser. No. 62/067,661 filed on Oct. 23, 2014, the entire contents of which are incorporated herein by reference.

BACKGROUND OF THE INVENTION

Avoidance of transfusion error in blood product administration is critical to patient safety. Mismatch of blood type (ABO/Rh) during transfusion can result in patient illness or death.

Use of technology to enhance the blood product selection protocol ensures the correct selection of each unit of blood for transfusion into each patient. The goal is to minimize the chance of human error in blood product type (ABO/Rh) selection as well as ensuring against outdated blood being selected. Giving medical professionals a more comprehensive search for blood product freshness and cross-match selection capabilities improves patient outcomes and in some cases will favorably impact patient survival.

SUMMARY OF THE INVENTION

The system has one or more tray assemblies each with a plurality of bins to hold biological fluid containers for computer-directed assignment to patients in response to authorized orders. These may include any biological fluid including blood products, parental drugs, stem cells or even breast milk. For exemplary purposes, an embodiment wherein the containers described are blood product containers and the tray assemblies are stored on shelves or in drawers within a hospital refrigerator. Other configurations, such as platelet bags in a warmer unit are functionally equivalent.

The primary function of the system is to provide a real-time interface between a physician, nurse or technician and a blood product storage system to ensure that the correct blood product is selected for administration to the correct patient. This is especially important when blood is needed in emergency situations from local storage units in emergency rooms, trauma centers and surgical suites. By assisting the human element as much as possible in the blood product selection process, it will help to ensure that the correct blood product bag is selected for transfusion into the correct patient.

BRIEF DESCRIPTION OF THE DRAWINGS

The accompanying drawings, which are incorporated in and constitute a part of this specification, illustrate embodiments of the invention, where like reference numbers in the drawing figures refer to the same feature or element and may not be described in detail for every drawing figure in which they appear and, together with a general description of the invention given above, and the detailed description of the embodiments given below, serve to explain the principles of the invention.

DETAILED DESCRIPTION

Before any embodiments of the invention are explained in detail, it is to be understood that the invention is not limited in its application to the details and construction and the arrangement of components set forth in the following description, or illustrated in the following drawings. The invention is capable of other embodiments and combinations of hardware, software and electronics which are functionally equivalent within the scope of the claims set forth below.

The key elements of this system are tray assemblies used in a storage system which detect and hold radio frequency identification (RFID) tagged biological fluid containers and a local fluid management computer system which maintains a real-time database of the local refrigerator inventory and assists in assignment of specific biological fluid units in the inventory to specific patients in response to authorized orders, such as physician transfusion orders.

The invention incorporates the following functionalities:

Auto-Discovery: Capability for real-time updating of local refrigerator inventory transactions and requests for automatic replenishment from the central hospital biologic fluid storage, such as a blood bank.

Display Indicator: Next to each biological fluid container in each bin is a bin status indicator display to provide positive indications of a unit's status or selection for removal. Only the indicated authorized units can be removed from storage without an alarm.

Bedside Validation: Data may optionally be written in the RFID chip of the biological fluid container to provide a seamless validation of the assigned patient to ensure assignment of the correct unit for transfusion into the correct patient. Alternatively, data on the allocated biological fluid containers may optionally be communicated to the hospital information network enabling it to drive the bedside validation.

Resident Data: Data files containing detailed information about each biologic fluid storage container and its contents is resident on the database associated with the local biological fluid container system containing it. This way the information is always available at time of patient assignment.

Compatibility: Usable with the majority of industry software, such as blood banking software, for banks and hospitals. Using mirrored data volumes routine electronic blood type look up may be performed from with software from one or more software vendors.

Freshness Rotation: Due to the real-time nature and our ability to keep data directly on the unit, when blood type look up is performed it returns a display of available blood oldest first. A push button on the user interface may be applied to reorder the displayed inventory to freshest first.

Greater Search Criteria: Search and selection criteria are not limited to just the ABO blood group Communications: A wide variety of communications protocol, including the use of multiple systems in each data path.

Retrofitability: The tray assemblies may be easily retrofit into existing blood storage refrigerators. Tray assemblies may be battery powered and charged wirelessly via an inductive battery chargers. Wireless communications with each tray assembly avoids the need for communication wiring to each tray assembly.

The system has one or more tray assemblies each with a plurality of bins to hold biological fluid containers. Since many biological fluids required control temperatures, it is assumed that these tray assemblies are mounted in either a refrigerator or warmer as required to maintain proper storage temperature of the biological fluids. For exemplary purposes, an embodiment directed towards biological fluid containers that are blood product containers, typically blood bags, and the tray assemblies are on shelves or in drawers within a biological fluid storage refrigerator such as a hospital storage refrigerator. Other configurations, such as platelet bags in a warmer unit are functionally equivalent.

Figure 1:
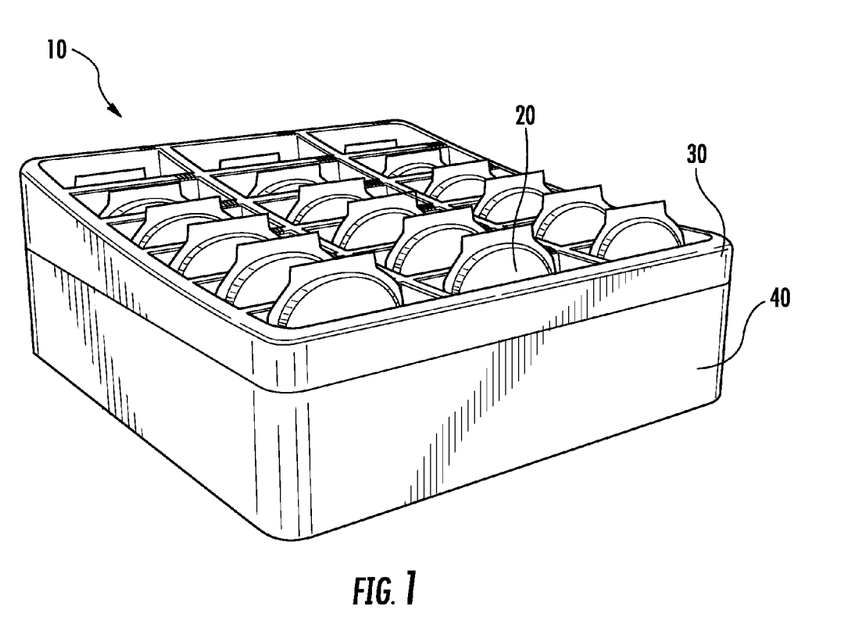
FIG. 1 is a schematic perspective view of an exemplary tray assembly containing a plurality of blood product bags.

FIG. 1 illustrates an example of a tray assembly system 10 which contains a plurality of biologic fluid containers 20, here dimensioned for use with biological fluid containers 20 provided as standardized blood bags. In this embodiment the tray assembly 10 consists of two major components: a tray base 40 with a tray insert 30 which forms the individual bins used to hold the biologic fluid containers 20.

Figure 2:
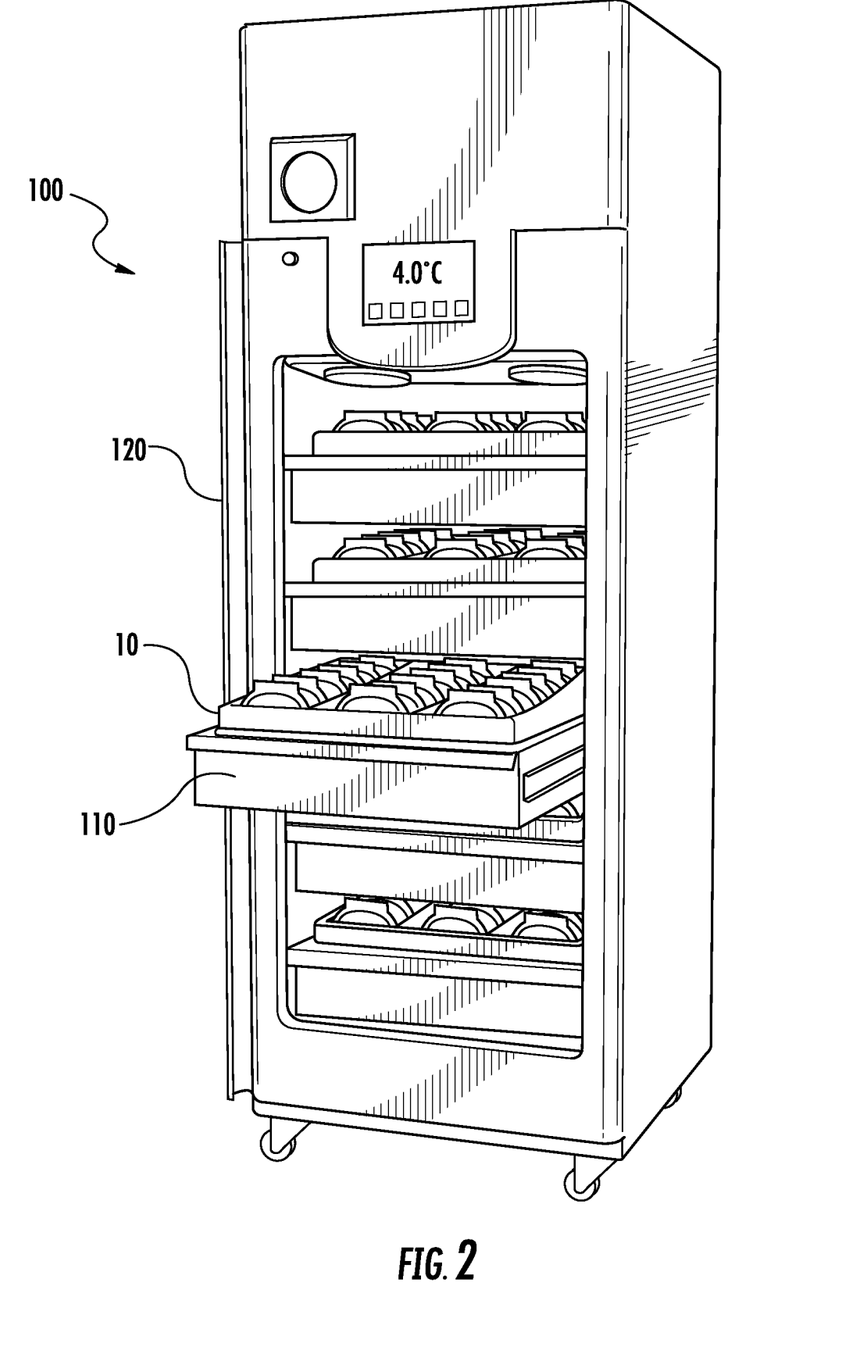
FIG. 2 shows a schematic isometric view of a tray assembly as installed in the drawer of a biologic fluid storage refrigerator.

FIG. 2 illustrates multiple tray assemblies 10 mounted in drawers 110 within a typical biologic fluid storage refrigerator 100. In this embodiment the biologic fluid storage refrigerator 100 consists of a plurality of drawers 110 into which tray assemblies 10 are mounted. In other typical refrigerator 100 embodiments, the tray assemblies 10 may be set on shelves which may or may not pull out for access. A typical implementation would encompass multiple tray assemblies 10, one for each pull-out drawer or each fixed or pull-out shelf of the biologic fluid storage refrigerator 100. The biologic fluid storage refrigerator 100 may have a closable refrigerator door 130 (best shown in FIG. 8).

Figure 3:
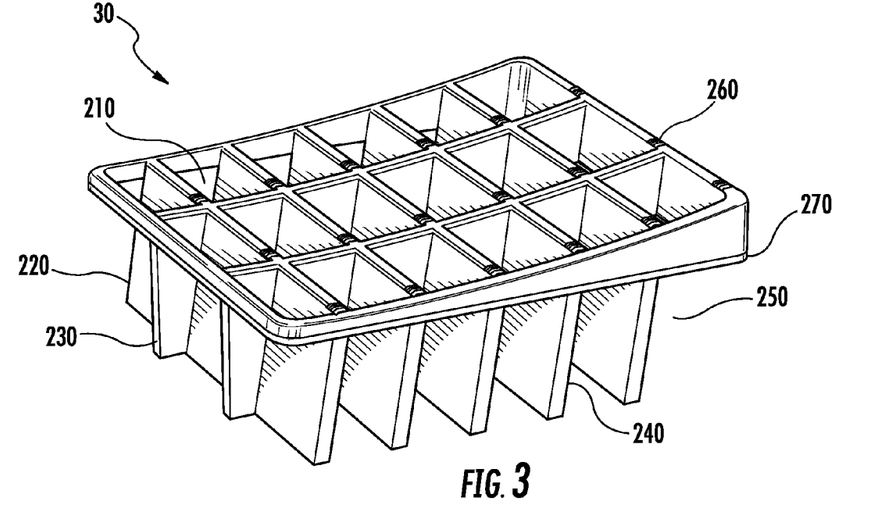
FIG. 3 is a schematic perspective view of the tray assembly grating used to form the tray assembly bins for storage of biologic fluid products.
Figure 4:
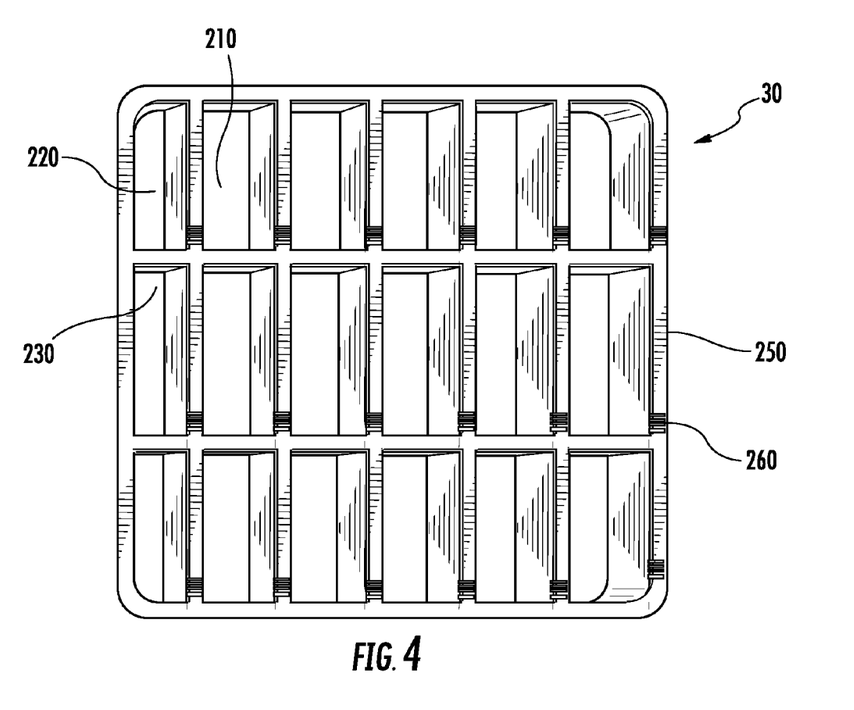
FIG. 4 is a schematic top view of the tray assembly grating shown in FIG. 3.

FIG. 3 shows a tray insert 30, which may be, for example, injection molded, although other methods of fabrication including 3D printing may be utilized which produce a functional equivalent. The tray insert 30 is built with a plurality of lateral separators 220 and a plurality of lineal separators 230 in orthogonal directions to form a plurality of bins 210. FIG. 4 shows the same tray insert 30 from above. Note that the lateral separators 220 have one straight surface and one surface preferably at an angle to the vertical so that the blood bags in each bin will lie flat against the angled surface. In the preferred embodiment, below elevation 270 which is even with the top of drawer 110 as shown in FIG. 2, the tray assembly 10 sits within drawer 110, and only the portion of tray assembly 10 is exposed above drawer 110, as may be seen in FIG. 2.

Although not shown, each of the bins 210 has an RFID bin antenna assembly 240 mounted on one wall next to the blood bag, typically on the rear angled bin wall against which the blood bag lies. In this manner a nearly constant distance is maintained between each bin antenna assembly 240 and the RFID tag 330 on the blood bag. To prevent a bin antenna assembly 240 from communicating with the blood bag behind it, a metal shield or ferrite patch may be placed behind the RFID antenna circuits as part of the bin antenna assembly 240 to direct signals only forward to the blood bag with the bin in which it is in contact.

Although not shown explicitly in these drawings, the separators 220 and 230 may be hollow to permit bin antenna assembly wiring and bin status indicator display wiring (or alternatively, fiber-optic light pipes) to be connected to each bin 210 from the hollow circuitry area 250 behind the rear lateral separator. An example of operator visual feedback appears as status indicator display 260 in both FIG. 3 and FIG. 4. The circuitry area 250 contains the RFID antenna multiplexers and RFID reader boards; the tray controller, and in the preferred embodiment wireless communications to a master antenna located inside the refrigerator rather than wired communications. Any wireless connection technique including but not limited to Wi-Fi, Bluetooth or ZigBee may be employed. The tray controller utilizes this wired or wireless connection for two-way communications either directly or over a local area network to the fluid management computer 500.

Figure 5:
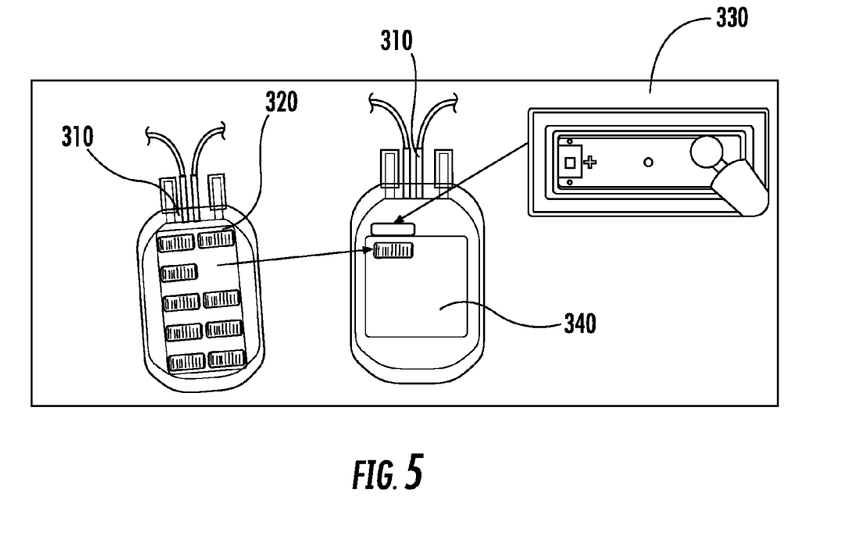
FIG. 5 shows an exemplary barcode label and an RFID tag as mounted on an empty biologic fluid container.

FIG. 5 shows a typical 13.56 MHz (HF) RFID tag 330 mounted on a blood product container 310. The preferred embodiment utilizes standard ISO 15693 or ISO 18000-3 mode 1 RFID tags operating at 13.56 MHz on the blood bag as part of the iTRACE™ RFID system for blood product identification. The iTRACE™ system was developed at the BloodCenter of Wisconsin and approved for use in the United States under an FDA 510(k). In iTRACE, an RFID tag is used to augment the barcode labeling by storing the same key data structures in the tag which are on placed the bag during final labeling in the form of, for example, International Society for Blood Transfusion ISBT 128 barcodes.

In an FDA-approved iTRACE RFID tagging system, an ISBT 128 Donation Identification Number (DIN) barcode label 320 is typically taken from a pre-printed label set 310 and placed in the upper left-hand corner of the base label 340 on blood bag 310. An RFID label is typically placed above it on the blood bag, and typically the DIN barcode label is then read and it's DIN written into the RFID tag.

During final labeling, the key blood bag information is encoded both in the RFID tag and on barcodes on the blood bag label using, for example, ISBT 128 data formats, including at least four pieces of information typically utilized to ensure safe transfusion:
1) The Donation Identification Number (DIN),
2) The ABO/Rh blood group,
3) The ISBT 128 Product Code and
4) The ISBT 128 Expiration Date (which optionally may include a time of day) of the blood product.

Other types of bar codes, RFID tags and RFID tag data encoding formats alternately may be used, depending, for example, upon the government regulatory restrictions in the country of use.

Figure 6:
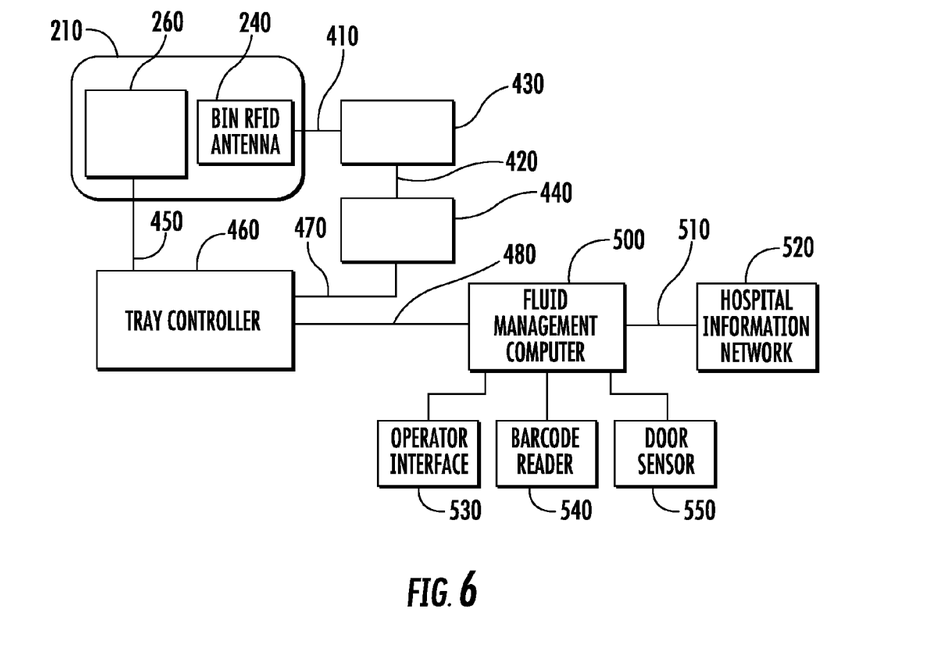
FIG. 6 shows a schematic block diagram of the electronics, communications links and computer systems used.

FIG. 6 shows a block diagram of the electronics and data processing system utilized within and attached to each tray assembly. Each bin 210 corresponding to tray insert 30 on the tray assembly 10 is comprises a specific bin status indicator display 260 and a specific bin antenna assembly 240. A plurality of bin antenna assemblies 210 may be connected using antenna connections 410 to one or more optional antenna multiplexer 430 which is connected using reader-multiplexer connection 420 to an RFID reader(s) 440. Alternatively, a bin antenna assembly 240 may be connected directly to its own RFID reader 440. Each RFID reader 440 is connected by a reader-controller connection 470 to the tray controller 460. The tray controller 460 is also connected via bin status display connections 450 to the bin status indicator displays 260. In its simplest form, bin status indicator display 260 comprises a number of colored indicators whose selection and interpretation may be applied, for example, as described below. Alternate forms of bin status indicator displays 260 including graphical, icon or text displays are equivalent embodiments.

Tray controller 460 is bidirectionally connected to fluid management computer 500 utilizing one or more communications technologies 480 including a direct wired connection; a peer-to-peer wireless connection technology which includes but is not limited to Bluetooth or ZigBee as examples; or a wireless or wired local area network. Wireless communication between the tray controllers and the fluid management computer system may be enabled through use of repeater antennas mounted inside the refrigerator which are externally connected to the antenna of an external wired or wireless communications system.

The fluid management computer 500 and its operator interface 530 and optional barcode reader 540, are typically located near the biologic fluid storage refrigerator 100. The fluid management computer 500 may be standalone or optionally connected to an information system 520, such as a hospital communications network, over a communications path 510 which is typically a wired or wireless local area network.

Figure 7:
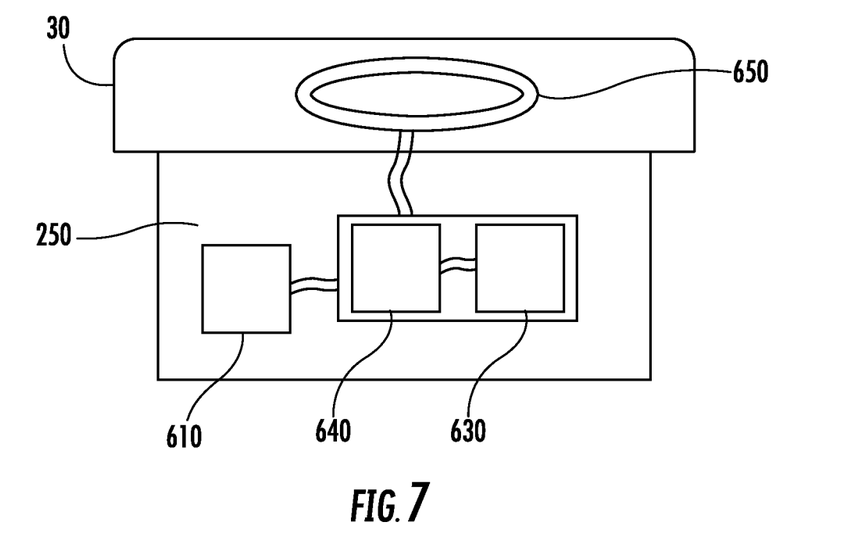
FIG. 7. shows a schematic diagram of the wireless induction power system of the tray assembly.

FIG. 7 is a rear view of tray insert 30. The contents of hollow circuitry area 250 are show below elevation 270, comprising electronics 610 connected to a rechargeable battery system which comprises rechargeable battery 630 and charging control electronics 640. Electronics 610, which may be a single package or a series of components distributed throughout tray insert 30, comprises tray controller 460, RFID reader(s) 440 and antenna multiplexer(s) 430, and their antenna connections 410 to the bin RFID antennas 240, reader-multiplexer connections 420 between the antenna multiplexers(s) 430 and RFID reader(s) 440, reader-controller connection(s) 470, and bin status display connections 450 to the bin status indicators 260.

Electronics 610 may be directly powered through a direct wired connection to an external power source. In the preferred embodiment, a wireless power connection to the tray assemblies 10 is enabled when each tray assembly 10 is battery powered using rechargeable battery system comprising rechargeable battery 630 and charging control electronics 640. The charging control electronics 640 is connected to at least one tray induction coil 650, which typically mounts on the tray insert 30 above elevation 270, above the lip of drawer 100.

Figure 8:
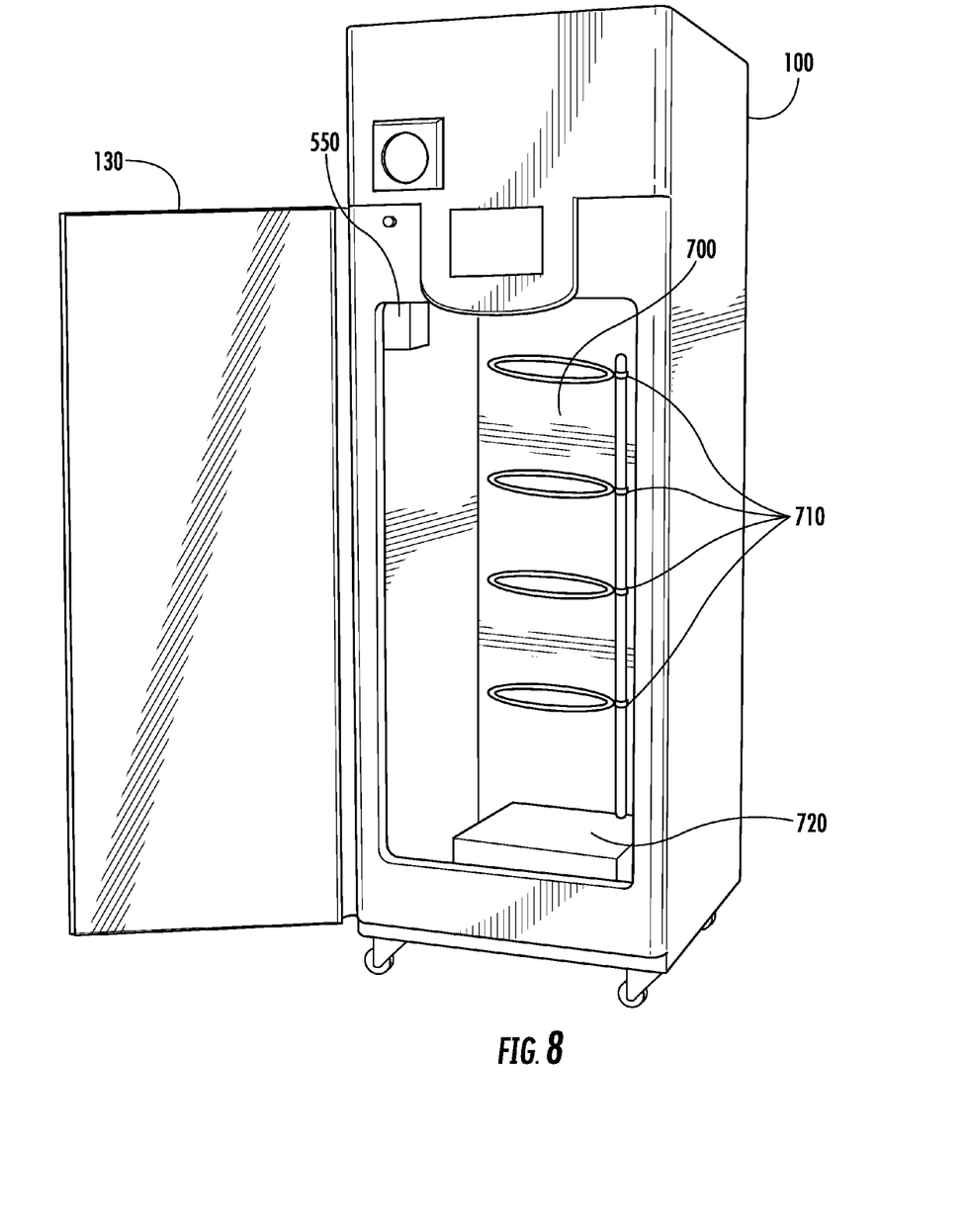
FIG. 8. shows a schematic diagram of the refrigerator portion of wireless induction power system for the trays.

When the drawer 110 is closed, a refrigerator induction coil or a plurality of coils 710 as shown in FIG. 8 mounted on the interior refrigerator wall 700 of biological fluid storage may be closely aligned with the tray induction coil or coils 650 of the tray assembly 10 in said drawer 110, for inductive power coupling between the tray assembly 10 and the refrigerator wall 700. To maximize RF power transfer, it is preferred that both refrigerator induction coils 710 and tray inductions coil 650 are both resonant at the RF excitation frequency of the induction power exciter 720. Power is transferred from induction power exciter 720 through refrigerator induction coils 710 to tray induction coils 650 and there through to the charging control electronics 640 to enable recharging of the rechargeable battery 630 in tray assemblies 10. This allows wireless electrical powering of the battery-operated tray assemblies 10.

The system operation will now be discussed. Biological fluid containers 20 (here Blood bags 310) with encoded RFID tags 330 may be placed into any available bin 210 in a tray assembly 10 in the biologic fluid refrigerator 100. When blood does not come to the hospital from the blood processing center with preinstalled and/or pre-encoded RFID tags 330, the system described herein has the capability at the operator interface 530 of the fluid management computer 500 for an operator to place an RFID tag 330 directly on the blood bag 310, read the blood bag ISBT 128 barcodes on the blood bag using barcode reader 540 and encode an RFID tag 330 on the blood bag 310. RFID tag data format may be according to standardized systems such as that used in iTRACE™ in the blood processing centers.

When the refrigerator 120 door of the biologic storage refrigerator 100 is shut, such may be sensed by the fluid management computer 500 using door sensor 550, and preset business rules may be executed and/or evaluated. For example, a cycle may be initiated to scan all bins 210 of all tray assemblies 10 in the biologic storage refrigerator 100 to determine any changes made to the biologic storage refrigerator 100 contents. Empty bins 210 may be identified, and information from the RFID tags 330 of all populated bins 210 automatically read and entered into an inventory database on the fluid management computer 500 to reflect the current fluid storage refrigerator 100 contents. Any outdated blood units 310 may be identified on the operator interface 530 for removal by the operator.

Further, when a patient transfusion order is received at the fluid management computer operator interface 530, it may be entered either as an electronic record transmitted directly by the hospital information network or by the operator manually and/or locally scanned from paperwork.

Optionally, if for this transfusion request, specific cross matching beyond ABO/Rh is required, messages may be exchanged with the hospital information network to determine if the specific blood bags in that local biologic storage refrigerator 100 inventory have an acceptable cross-match.

One or more blood bags 310 of the matching blood type may be found in the biologic storage refrigerator 100 inventory. Default blood selection by Expiration Data is the oldest unit of that type; however, in special situations such as transplant surgery or dire medical conditions the freshest unit of that type may be alternatively selected. When a unit of the matching blood type cannot be found, and when permitted by the prescribing physician, compatible units may be suggested for operator selection. For example, AB-blood type is very rare; compatible types A−, B− or O− may be available and when permitted are displayed for operator selection.

An error message may be generated at the operator interface 530 when sufficient blood of the correct type is not available in the biologic fluid storage refrigerator 100. A message may also be optionally sent to the hospital information network to request immediate delivery of the needed blood type from the hospital or an external blood bank.

The operator final selection and blood bag assignment process and transfusion order may each be recorded as a database transaction. The operator interface 530 tells the operator in which refrigerator drawer to look in for the assigned blood bag 310. The bin status indicator display 260 for each bin 210 will be set to red except for the bin 210 containing the assigned blood bag, which is indicated in green. The RFID system is now activated. The operator takes the assigned blood bag from that bin 210, and the RFID system verifies that the assigned bin 210 is now empty. An alarm may sound, for example, if blood has been taken from the wrong bin 210 or additional unassigned products are removed.

The blood inventory database with its now-attached transfusion and selection data record is now updated. An optional request may also be communicated to the hospital blood bank for replenishment of the refrigerator, especially for critical emergency use blood types such as type O Rh negative.

To enable a check at the patient bedside of a 3-way match of the patient ID number, transfusion order number and key blood bag ISBT 128 data of the assigned units, one of two optional methods may now be employed. The first optional method consists of writing specific patient-related and/or transfusion order information to the RFID tag on said selected blood product container(s) for offline bedside verification. The second method requires that the fluid management computer send the complete blood unit assignment transaction record for the assigned bags to enable hospital information system-driven bedside verification.

Many modifications to and other embodiments of the invention set forth herein will come to mind to one skilled in the art to which these inventions pertain, once having the benefit of the teachings in the foregoing descriptions and associated drawings. Therefore it is understood that the inventions are not limited to the specific embodiments disclosed, and that modifications and other embodiments are intended to be include within the scope of the appended claims. Although specific terms are employed herein, they are used in a generic and descriptive sense only and not for purpose of limitation.

We claim:

1. A biological fluid container identification, tracking and selection system comprising:
    a tray assembly comprising a plurality of bins, each of said bins configured to support storage of one or more biological fluid containers;
    the biological fluid containers provided with radio frequency identification ("RFID") tags;
    an electronic tray controller coupled to a rechargeable battery;
    a charging control electronics configured for charging the rechargeable battery;
    a tray induction coil receiving power by magnetic induction coupling and supplying power to the charging control electronics;
    a bin status indicator display for each bin, the bin status displays coupled to said electronic tray controller;
    an RFID bin antenna assembly for each bin, the RFID bin antenna assembly coupled to one or more RFID reader each of which are connected to said electronic tray controller;
    a fluid management computer with an operator interface, where the fluid management computer is in communication with the electronic tray controller of each tray assembly;
    whereby the electronic tray controller is able to utilize the RFID reader to detect whether or not the RFID tag of one of the biological fluid containers is within one of the bins, and able to read data from and optionally write data to the RFID tag on a biological fluid container within that bin.

2. The system of claim 1 wherein the electronic tray controller can communicate RFID tag information on a biological fluid container located in any bin to said fluid management computer.

3. The system of claim 1 where through the use of said operator interface connected to said fluid management computer, one or more biological fluid containers may be authorized by said fluid management computer according to a set of preset business rules.

4. The system of claim 1 wherein the tray controller can configure each bin status indicator display according to the communication with the fluid management computer.

5. The system of claim 1 wherein each biological fluid container is a blood product container and the RFID tag on the biological fluid container includes information comprising at least the International Society for Blood Transfusion (ISBT) ISBT data structures for Donation Identification Number, ABO/Rh Group, ISBT Product Type and Product Expiration Date.

6. The system of claim 1 wherein the RFID tag has been applied to the biological fluid container and/or programmed prior to insertion of said biological fluid container into a bin in a tray assembly.

7. The system of claim 6 wherein the RFID tag on biological fluid container is programmed by said fluid management system based upon the reading the contents of a barcode label on the biological fluid container.

8. The system of claim 1 wherein the tray assembly is within a biologic fluid storage refrigerator.

9. The system of claim 1 wherein the tray controller can communicate information read from the RFID tag to an information system through a communications path utilizing said fluid management computer.

10. A method of identifying, tracking and selecting a biological fluid, the method comprising:
    providing a radio frequency identification ("RFID") tag to a biological fluid container, said RFID tag carrying information regarding the contents of the biological fluid container;
    detecting the presence or absence of each biological fluid container within a bin on a tray assembly containing a plurality of bins, each of the bins provided with a bin status indicator display;
    reading the RFID tag on said biological fluid container under control of a tray controller coupled to a rechargeable battery charged by a charging control electronics receiving power from a tray induction coil; the tray induction coil receiving power by magnetic induction coupling;
    communicating the RFID tag information from the tray controller to a fluid management computer using communications technologies;
    displaying information on the bin status indicator display of the bin with a selected biological fluid container therein according to information received from a fluid management computer using communications technologies.

11. The method of claim 10 further comprising utilizing the fluid management computer to verify the information, and through preset business rules on the fluid management computer to determine if one or more of the biological fluid container are authorized; and
    selecting one or more biological fluid containers which are authorized.

12. The method of claim 11 further comprising the writing of information to the RFID tag on said selected biological fluid container.

13. The method of claim 10 wherein the biologic fluid containers contains blood products.

14. A tray assembly comprising:
- a tray controller coupled to a rechargeable battery; the rechargeable battery configured for recharging utilizing magnetic induction coupling;
- a plurality of bins, each of the bins configured for storage of a biological fluid container;
- one or more radio frequency identification ("RFID") readers connected to said tray controller through a controller port; and
- a bin antenna assembly associated with each bin;
- the bin antenna assemblies coupled with an RFID reader for detection of a biological fluid container within each of the bins, and to read and optionally write information to an RFID tag of any biological fluid container within each of the bins;
- the tray controller capable of external communication through a communications technology.

15. The tray assembly of claim 14 wherein each of the bins has an associated bin status indicator display connected to the tray controller.

16. The tray assembly of claim 14, wherein the tray assembly is positioned within a biologic fluid storage refrigerator.

* * * * *